United States Patent [19]

McIntire

[11] 4,185,090
[45] Jan. 22, 1980

[54] CHEMICALLY MODIFIED ENDOTOXIN IMMUNIZING AGENT

[75] Inventor: Floyd C. McIntire, Waukegan, Ill.

[73] Assignee: Abbott Laboratories, North Chicago, Ill.

[21] Appl. No.: 807,758

[22] Filed: Jun. 17, 1977

Related U.S. Application Data

[60] Division of Ser. No. 468,624, May 9, 1974, Pat. No. 4,057,685, which is a continuation of Ser. No. 223,012, Feb. 2, 1972, abandoned, which is a continuation-in-part of Ser. No. 147,686, May 27, 1971, abandoned, which is a continuation-in-part of Ser. No. 20,834, Mar. 18, 1970, abandoned, which is a continuation-in-part of Ser. No. 784,174, Dec. 16, 1968, abandoned.

[51] Int. Cl.$^2$ .................. A61K 31/73; C07H 5/06; C08B 37/00
[52] U.S. Cl. .................................. 424/92; 424/88; 424/94; 424/180; 536/1; 536/18; 536/119; 260/112 R
[58] Field of Search ..................... 424/92, 88; 536/1

[56] References Cited

U.S. PATENT DOCUMENTS 3,600,378  8/1971  Marsh et al. ........................ 536/1

OTHER PUBLICATIONS

McIntire et al., Biochemistry, vol. 6, No. 8, pp. 2363-2372, Aug. 1967.

*Primary Examiner*—Johnnie R. Brown
*Attorney, Agent, or Firm*—Robert L. Niblack; Gildo E. Fato

[57] ABSTRACT

A bacterial endotoxin lipopolysaccharide of reduced toxicity covalently coupled to a protein antigen exhibits enhanced adjuvant effects. The coupling was affected by reaction with haloacylhalide. Lipopolysaccharide acylated with an anhydride of a dibasic acid is detoxified; in combination with endotoxin polysaccharide covalently coupled to protein antigen it developed synergistic immunogenic effects.

5 Claims, No Drawings

CHEMICALLY MODIFIED ENDOTOXIN IMMUNIZING AGENT

CROSS-REFERENCE TO RELATED APPLICATIONS

This is a division, of application Ser. No. 468,624, filed May 9, 1974, now U.S. Pat. No. 4,057,685, issued Nov. 8, 1977, which is continuation of Ser. No. 223,012, filed Feb. 2, 1972, now abandoned, which is a continuation-in-part of Ser. No. 147,686, filed May 27, 1971, now abandoned, which is a continuation-in-part of Ser. No. 20,834, filed Mar. 18, 1970, now abandoned, which is a continuation-in-part of Ser. No. 784,174, filed Dec. 16, 1968, now abandoned.

DETAILED DESCRIPTION OF THE INVENTION

This invention relates to an improved immunizing agent and a method for its preparation. More particularly, it relates to a bacterial endotoxic lipopolysaccharide (LPS) chemically modified to destroy its toxicity while retaining its ability to stimulate antibody formation in warm-blooded animals and to a method for the preparation of the modified LPS.

It is well known that lipopolysaccharides from gram negative bacteria enhance the antibody response in warm-blooded animals to relatively pure protein antigens when the LPS and protein are injected either together or within an appropriate time interval. In rabbits, the LPS must be administered 0–48 hours after the antigen; in Balb mice, the LPS may be administered up to seven days before or eight days after the antigen and still show an enhancement of antibody formation. Such an agent which enhances antibody formation when associated with an antigen may be termed an "adjuvant", and the resulting phenomenon may be called an "adjuvant effect". Although the use of LPS as an adjuvant is highly desirable, its application has heretofore been somewhat limited by the toxicity of the LPS when administered in an effective dose. It would be desirable if the enhancement activity could be maintained while reducing the toxicity, or at least if the spread between the enhancement dose and the toxic dose could be increased.

It is an object of this invention therefore, to provide an LPS-adjuvant composition which provides an increased measure of antibody formation with reduced toxicity response. Another object of this invention is the provision of a chemically modified LPS adjuvant of reduced toxicity. A still further object of this invention is the provision of an adjuvant composition comprising a synergistic combination of chemically modified endotoxin derivatives of high antibody formation enhancement activity and low toxicity. A still further object of this invention is the provision of a method of chemically modifying LPS and an LPS derived fraction to reduce or eliminate the toxicity while maintaining its ability to enhance antibody formation.

These and other objects of the invention are achieved in part through the discovery that enhancement of antibody formation is greatly improved through chemically, covalently, bonding the antigen to the LPS. It has further been discovered that the LPS itself can be chemically modified to greatly reduce its toxicity while maintaining the antibody enhancement effect unchanged or only slightly diminished. Additionally, it has been discovered that a combination of chemically modified LPS derivatives cause more than additive adjuvant effects but without additive toxicity thereby producing an unexpected increased in the ratio of enhancement activity to toxicity.

Lipopolysaccharides have not been completely characterized but are believed to comprise a backbone of heptose disaccharide units joined together by phosphodiester bridges. Polysaccharides and fully acylated small aminohexose polymers are linked to the heptose disaccharide units. The LPS obtained from *E. coli* K-235 also has attached amino acids and ethanolamine which provide free primary amino groups that can be used in covalently linking the LPS to protein. Most of the fatty acid residues are in ester linkages and can be removed by very mild alkaline hydrolysis. Their preparation is well known in the art. They are also known to be soluble in a combination of anhydrous hydrogen bond-breaking solvents such as formamide, methylformamide, dimethylformamide, pyridine, picoline and the like.

In one embodiment of the invention, the active amino groups and possibly some hydroxy groups of an appropriate lipopolysaccharide are reacted with a haloacyl halide. Subsequently, the halogen of the haloacyl moiety is reacted with active sites on a protein antigen to provide a LPS covalently coupled to an antigen (LPS-A) through an ester or amide linkage. The reactions take place at about room temperature, that is at from about twenty to about fifty degrees centigrade, and in a medium with a pH above 7, preferably in one maintained at a pH of from about 8.5 to about 9.5.

The term "acyl" as used herein refers to acetyl, propionyl, butyryl and valeryl. The term "halo" refers to bromo, chloro, fluoro and iodo.

More particularly, the amino groups are reacted with, for example, bromoacetylbromide in aqueous solution as follows:

$$\text{lipopolysaccharide-(NH}_2)_x + (\text{Br}-\overset{\overset{\displaystyle O}{\|}}{C}-\text{CH}_2\text{Br}) \text{ excess}$$

$$\downarrow \text{pH 9}$$

$$\text{lipopolysaccharide-(NH}-\overset{\overset{\displaystyle O}{\|}}{C}-\text{CH}_2\text{Br})_x$$

The $$-\text{NH}-\overset{\overset{\displaystyle O}{\|}}{C}-\text{CH}_2\text{Br}$$

group is relatively stable, and the lipopolysaccharide (LPS) derivative can be separated from salts and excess reagent by dialysis. Each bromine atom of this LPS derivative can react with-SH and imidazole at about pH 7, or —NH$_2$ groups of proteins at about pH 8 to 10 to form:

$$\text{LPS}-\text{NH}-\overset{\overset{\displaystyle O}{\|}}{C}-\text{CH}_2-\text{S-protein}$$

$$\begin{array}{c}\text{CH}=\!=\!\text{CH-protein}\\ | \quad\quad |\\ -\text{N}\diagdown\quad\diagup\text{N}\\ \quad\text{C}\\ \quad\text{H}\end{array}$$

—NH-protein

Accordingly, any lipopolysaccharide with free amino groups may be coupled to any protein or other macromolecule, virus or cell fraction which has availabe —SH, imidazole or —NH$_2$ groups.

In another embodiment of this invention, an LPS derivative of greatly reduced lipid content (PS) is treated with haloacyl halide and protein antigen as above to provide coupled polysaccharide-antigen (PS-A) which has low toxicity and low adjuvant effect. To this is added an LPS which has been detoxified by reaction with the anhydride of a loweralkyl dibasic acid. In a preferred embodiment the reaction is conducted under conditions sufficient to acylate all free amino and approximately half of the free hydroxyl groups. The acylated lipopolysaccharide (AcLPS) itself has some adjuvant effect and very low toxicity but when mixed with the PS-A, the combination produces a greater than additive adjuvant response with far less than additive toxicity.

Anhydrides which may be used for this acylation are those which form half esters with the hydroxyl groups of the lipopolysaccharide molecule without replacing a substantial number of the fatty acid moieties originally present. Suitable anhydrides include compounds of the formula

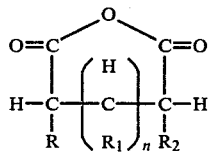

wherein n is an integer from 0 to 1, R, R$_1$ and R$_2$ represent hydrogen, C$_1$-C$_6$ alkyl, C$_2$-C$_6$ alkenyl, C$_5$-C$_6$ cycloalkyl, phthalyl or methylphthalyl, wherein any two R groups taken together can form a saturated or unsaturated cyclic substituent. Included among the above mentioned anhydrides are succinic anhydride, glutaric anhydride, 1,2-cyclohexane dicarboxylic anhydride and aromatic anhydrides such as phthalic anhydride and methylphthalic anhydride and their derivatives. The presently preferred anhydrides are the phthalic, methylphthalic and succinic anhydrides. Of course those anhydrides which disproportionately increase toxicity of the LPS derivatives relative to its adjuvant effect are to be avoided. Salts of the acylated lipopolysaccharide may also be prepared and the water soluble salts such as the sodium, potassium, lithium and amine salts are especially preferred although other salts are also useful.

The term "C$_1$-C$_6$ alkyl" refers to both straight and branched chain alkyl groups and includes methyl, ethyl, n-propyl, iso-propyl, n-butyl, sec-butyl, tert-butyl, n-pentyl, iso-pentyl, n-hexyl and the like.

The term "C$_2$-C$_6$ alkenyl" refers to C$_2$-C$_6$ alkyl groups as defined above, from which a hydrogen has been removed from each of two adjacent carbon atoms to produce vinylenic unsaturation; e.g., vinyl, allyl, methallyl, 1-pentenyl and the like.

The acylation reaction is conducted at about room temperature, desirably below about 50° C., and in any event below the temperature at which substantial decomposition takes place. The reaction time is dependent upon the temperature and should be of sufficient duration to enable acylation of the hydroxyols. This may require from about 12 to about 30 hours and may be performed in one or more than one acylation steps. The details of the invention will be better understood from references to the following examples which are to be regarded as illustrative only and not limiting.

EXAMPLE 1

Preparation of Lipopolysaccharide (LPS) and Polysaccharide (PS)

Gram negative bacteria, E. Coli K-235 were grown on an aerated medium, centrifuged and extracted with aqueous phenol. The polysaccharide (PS) fraction of the LPS was obtained by hydroxylaminolysis. Details of the procedures are set forth by McIntire et al, Biochemistry, 6, 2363 (1967).

The LPS and PS so obtained were chemically modified as indicated in the following examples.

EXAMPLE 2

Preparation of Bromoacetyl LPS

One gram of LPS was suspended in 250 ml. ½ saturated sodium acetate in an ice bath and the pH was adjusted to 9 with sodium hydroxide; 200 μl of bromoacetylbromide dissolved in 10 ml. of dry reagent grade dioxane was added dropwise, and simultaneously 1 N NaOH was added at a rate sufficient to maintain the pH between 8.5 and 9.5. After addition of all the bromoacetylbromide, the pH was adjusted to approximately 4.5 with 6 to 12 N HCl. The preparation was dialyzed for 5 to 7 days at 4° C. in a cloth jacket tube. The bromoacetylated product is stable at the low pH, and may be either stored frozen or lyophilized. Its adjuvant activity is about equal to the LPS starting material. Bromine available for coupling was estimated by allowing the bromoacetylendotoxin to react with an equal weight of N-(2,4-dinitrophenyl)ethylenediamine at pH 9 for 12 to 20 hours at room temperature, with constant stirring. The solution was adjusted to pH 4, and dialyzed exhaustively against $10^{-4}$ N HCl; the amount of N-(2,4-dinitrophenyl)ethylenediamine bound was determined by the absorbance at 340 mμ. Bromine available for coupling as determined above was usually about 0.1 μM per mg. of endotoxin, although the amount found by elemental analysis was usually several fold higher. Most of the bromine "not available for coupling" could be removed by electrodialysis.

Bromoacetylated PS was prepared according to the same procedure, but substituting the PS of Example I for the LPS mentioned above. The amount of bromine available for coupling was usually about 0.04 μM per milligram of endotoxin.

The following example illustrates the coupling of the bromoacetylated products to a protein antigen of which various types may be employed.

EXAMPLE 3-A

Coupling of Antigen to Bromoacetyl LPS

One hundred mg. of bromoacetylendotoxin in 25 ml. H$_2$O, pH 4.5, was mixed with 100 mg. antigen in 20 ml. and 5 ml. of 1 M K$_2$HPO$_4$ was added. The antigen was a crystallized human serum albumin (HSA) preparation obtained from Pentex Incorporated. The solution was diluted at 100 ml., adjusted to pH 10 with 2 to 5 N NaOH, stirred at room temperature for four hours, and adjusted back to pH 7. Chromatography over G-200 Sephadex ® yielded two protein-containing peaks. The excluded (high molecular weight) peak contained LPS coupled to HSA and presumably some free LPS; the included peak was largely unreacted HSA. The degree of covalent coupling of HSA to LPS was determined by adjusting the solution to 0.15 M with sodium chloride, extracting three times at 65° C. with an equal volume of phenol, removing the phenol from the aqueous phase by three ether extractions, and measuring the protein in the aqueous phase. By this procedure mixed and not coupled LPS and HSA could be separated completely. At least 10% and usually 25 to 30% of the HSA was found to have been coupled to LPS by the method of this example.

EXAMPLE 3-B

The procedure of Example 3-A was repeated except that the bromoacetylendotoxin was replaced by an equal quantity of bromoacetyl polysaccharide prepared according to Example 2. More than about 10% of the antigen was coupled to the polysaccharide.

The following example illustrates the acylation of a lipopolysaccharide.

EXAMPLE 4

Preparation of Sodium Succinyl LPS

One gram of LPS and 10 g. of succinic anhydride were dissolved in 50 ml. of formamide and 50 ml. of pyridine which had been dried over sodium hydroxide pellets and redistilled. The reaction flask was sealed with a double layer of Parafilm ®, stirred at room temperature for 20 to 22 hours and poured into 200 ml. of pyrogen-free water. The solution was dialyzed at 4° C. against 5 liters of triple-distilled water for 48 hours, 0.1 M sodium bicarbonate 48 hours, triple-distilled water 48 hours, and the water was changed every 8 to 16 hours and was stirved constantly. To provide an increase in volume during dialysis, the tubing was placed inside a cloth jacket. The sodium succinyl LPS was concentrated and lyophilized. This product was succinylated again for 5 to 7 hours at room temperature with the same reagents and proportions. This final product yield was 1.85 to 2 grams. By acid-base titration it was 50 to 55% by weight sodium succinyl (NaOOCCH$_2$CH$_2$CO—), which is equivalent to about 8 micromoles per milligram of LPS in the product.

Adjuvant activity of the preparations of Examples 1–4 was determined on male Sprague Dawley strain rats weighing about 200 g., and male albino New Zealand rabbits weighing about 2 kg. Each rat received 0.05–0.5 mg. antigen in 0.25 mg. of saline; rabbits were injected with 0.04–0.8 mg. antigen in 0.5 ml. of saline. The adjuvant effect of LPS was demonstrable when administered by intraperitoneal, intramuscular or subcutaneous routes; injection into foot pads was no more effective than intramuscular (leg) or subcutaneous injections (nucha). Antibody estimation was by passive hemagglutination with serial two-fold dilution. Antibody titers were expressed as the reciprocal of the dilution. Each value in the tables represents the geometric mean of determinations from 8–12 rats.

EXAMPLE 5

Preparation of Sodium Phthalyl LPS

One gram of LPS was dissolved in 50 ml. of formamide and 15 g. of phthalic anhydride was dissolved in 50 ml. of dry, redistilled pyridine. The two solutions were mixed, the reaction flask was sealed with a double layer of Parafilin ®, and the solution was stirred at 28° C. After 24 hours of stirring, the reaction solution was diluted with an equal volume of pyrogen-free distilled water and dialyzed as in Example 4. Insoluble material was removed by filtration through a sintered glass pyrogen-free filter under a slight positive pressure with filtered air. The solution was concentrated and lyophilized. The yield of dry sodium phthalyl LPS was usually 2.5 grams from 1 gram of LPS.

EXAMPLE 6

Preparation of Sodium Methylphthalyl LPS

This material was prepared according to the procedure set forth in Example 5, using 4-methyl phthalic anhydride.

EXAMPLE 7

Preparation of Sodium Glutaryl LPS

This material was prepared according to the method of Example 4 except that 1.2 g. of glutaric anhydride was used in place of 1 g. of succinic anhydride and the second esterification was at 37° C. for 24 hours instead of room temperature for 7 hours.

While sodium succinyl is suitable in the practice of this invention, sodium phthalyl LPS, sodium methylphthalyl LPS and sodium glutaryl LPS are all more effective than sodium succinyl LPS in enhancing antibody formation to human serum albumin in the rat. The glutaryl derivative is more pyrogenic than the succinyl while the phathalyl and methylphthalyl derivatives are the least toxic and pyrogenic, as can be seen from Table 1.

TABLE 1

| Derivative | Ratio of Pyrogenicity[a] of LPS / Pyrogenicity of Derivative | Ratio of Toxicity[b] of LPS / Toxicity of Derivative | Antibody Titre[c] |
| --- | --- | --- | --- |
| succinyl | 10,000 | 1,000 | 40 |
| glutaryl | 1,000 | | 120 |
| phthalyl | 100,000 | 10,000 | 140 |
| methyl phthalyl | 100,000 | | 160 |
| 0.25 mg HSA coupled to 0.25 mg LPS | | | 140 |

[a]Pyrogenicity was measured in rabbits
[b]Toxicity was measured in actinomycin D-treated mice.
[c]Each rat received 3.1 mg. of sodium glutaryl, phthalyl, or methyl phthalyl LPS mixed with 0.25 mg. of HSA (human serum albumin). Five weeks after primary injection, each rat given sodium succinyl LPS received 2.5 mg. mixed with 0.25 mg. of HSA. The antibody is expressed as passive hemagglutination titre.

The following example illustrates the importance of covalent coupling between antigen and LPS when both are injected subcutaneously in the rat.

EXAMPLE 8

Antigen (human serum albumin) and LPS were injected into rats almost simultaneously in separate sites about one inch apart in the neck in the amount of 0.19 mg. antigen (A) in site 1 and 0.31 mg. LPS in site 2. Other rats received LPS-A coupled according to the procedure of Example 3 in the amount of 0.5 mg; also administered was antigen mixed with LPS immediately before injection in the amount of 0.19 mg. A mixed with 0.31 mg. LPS. The antibody level was determined weekly and was as reported in Table 2.

TABLE 2

| Dose | | Relative Immunologic Response WEEKS | | | | | |
|---|---|---|---|---|---|---|---|
| | | 1 | 2 | 3 | 4 | 5 | 6 |
| LPS and A separate sites | } 0.5 mg. | 0 | 1.5 | 2.6 | 0 | 0 | 1.5 |
| LPS plus A mixed | } 0.5 mg. | 3.4 | 2.6 | 7 | 15 | 10 | 19.5 |
| LPS Plus A coupled | } 0.5 mg. | 8.7 | 27 | 159 | 115 | 80 | 72 |

The data of Table 2 indicates clearly that under the conditions of this experiment, there was essentially no adjuvant effect unless LPS was mixed with antigen before injection, and that the effect was enhanced by coupling the two molecules. When, immediately before injection, the antigen was mixed with the bromoacetyl LPS of Example 2 at a pH of about 7 or less, which condition did not favor coupling, the results were the same as those obtained with a simple mixture of LPS and antigen. This means that bromoacetylation of LPS, per se, did not confer any unique adjuvant properties and that the superiority of LPS-A is indeed attributable to the coupling of the two olecules.

The increased adjuvant effect demonstrated above is of course a highly beneficial result. In a preferred embodiment of this invention, an equivalent immunogen response was achieved with a composition of reduced toxicity. The removal from the lipopolysaccharide of essentially all of the ester-linked fatty acids with no other known major change in the molecule reduced the pyrogenicity in the rabbit by a factor of 1,000,000 and reduced toxicity in the mouse by more than 6,000 fold. This polysaccharide fraction (PS) was able to neutralize almost all of the antibody to LPS in a rabbit antiserum to the parent bacteria.

The highly succinylated lipopolysaccharide (AcLPS) of Example 4 was less pyrogenic than LPS by a factor of more than 1,000 and less toxic in the mouse by more than 500 fold. It retained substantially all of the fatty acid moieties of LPS but it gave no indication of reacting with the specific antibody employed.

These chemically modified derivatives, PS and AcLPS, were each much less immunogenic than lipopolysaccharide coupled to antigen. The polysaccharide coupled to antigen of Example 3 gave very little primary response, but a secondary response indicated some activity.

The succinylated LPS of Example 4, from results of separate comparative determinations, was estimated to be about 1/100th as effective as LPS in enhancing the antibody response to A. However, its toxicity was at least 1,000 and possibly 10,000 times lower than that of LPS so that the ratio of toxicity to adjuvant effect has been decreased in the product of Example 4 by a factor of at least 10 and perhaps by as much as 100.

An important aspect of this invention resides in the descovery that a mixture of the acylated lipopolysaccharide of Example 4 with a low lipid polysaccharide prepared as described in Example 1 or preferably with the polysaccharide coupled to antigen produced according to Example 3 provides a very high adjuvant effect with very low toxicity. The combination of PS and AcLPS had no greater pyrogenicity than AcLPS alone. The high level of adjuvant effect achieved is illustrated in Example 6.

EXAMPLE 9

As was done in the experiment of Example 8, eight to twelve rats were each injected with a test composition and the antibody levels determined by a passive hemagglutination technique. The results are presented in Table 3 below. The materials for injection were selected to provide a constant quantity, 0.25 mg. of antigen, and were as follows:

| Test Number | Injection - in Saline |
|---|---|
| 20 | 05. mg. of the reaction mixture of Example 3-A in which about 25-30% of the antigen was coupled to the lipopolysaccharide to provide 0.25 mg. of antigen as a control. |
| 21 | A chromatographic fraction from the reaction mixture of Example 3-B sufficient to provide 0.25 mg. antigen and 0.45 mg. polysaccharide with about 30% of the antigen coupled to the polysaccharide, mixed with 2.5 mg. acylated lipopolysaccharide prepared according to the process of Example 4. |
| 22 | A mixture of 0.25 mg. antigen, 0.25 mg. polysaccharide and 2.5 mg. of the acylated lipopolysaccharide of Example 4. |
| 23 | A mixture of 0.25 mg. antigen and 2.5 mg. of the acylated lipopolysaccharide of Example 4. |
| 24 | A chromatographic fraction from a quantity of the reaction mixture of Example 3-B sufficient to provide 0.25 mg. antigen and 0.45 mg. polysaccharide with about 30% of the antigen coupled to the polysaccharide. |

TABLE 3

| Test Number | Dose | | Immunologic Response Geometric Mean Hemagglutination Titer | | | | | |
|---|---|---|---|---|---|---|---|---|
| | | | Weeks 1 | 2 | 3 | 4 | 5 | 6 |
| 20 | 0.25 mg. antigen (25%-30% coupled) 0.25 mg. LPS | | 5.7 | 3.5 | 14 | 91 | 92 | 63 |
| 21 | 0.25 mg. antigen (25% coupled) in PS-A 2.5 mg. AcLPS | } mixed | 0 | 6.6 | 15 | 65 | 69 | 43 |
| 22 | 0.25 mg. antigen 0.25 mg. PS 2.5 mg. AcLPS | } mixed | 0 | 1.9 | 5.6 | 37 | 46 | 37 |
| 23 | 0.25 mg. antigen 2.5 mg. AcLPS | } mixed | 0 | 2.4 | 2.5 | 15 | 30 | 25 |
| 24 | 0.25 mg. antigen (25% coupled) in PS-A | | 0 | 0 | 0 | 3.4 | 2.2 | 0 |

Statistical analysis indicated the results of tests numbered 20 and 21 do not differ significantly.

Tests 23 and 24 disclose the level of adjuvant response produced individually by each of the chemically modified lipopolysaccharide derivatives. Test 21 shows the surprisingly great response demonstrated by a mixture of the derivatives. This immunologic response is statistically equivalent to that of lipopolysaccharide coupled to antigen (LPS-A) but with at least 1,000 fold less toxicity (pyrogenicity).

I claim:

1. An ingredient for an immunizing agent comprising a protein antigen covalently coupled to a bacterial endotoxin partially detoxified lipopolysaccharide, said protein antigen having available —SH, imidazole or —NH$_2$ groups and said lipopolysaccharide having free amino groups.

2. An ingredient for an immunizing agent comprising a protein antigen covalently coupled to a bacterial endotoxin haloacetylated polysaccharide.

3. The method of generating an immunologic response in a warm-blooded animal comprising administering to said animal a bacterial endotoxin lipopolysaccharide covalently coupled to a protein antigen in an amount sufficient to develop an antibody response in said animal, said lipopolysaccharide having at least one free amino group and an anhydride selected from the group consisting of compounds of the formula

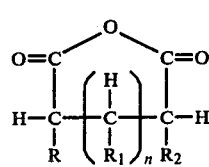

wherein n is 0 or 1, and R, $R_1$ and $R_2$ each represent hydrogen, $C_1$-$C_6$ alkyl, $C_2$-$C_6$ alkenyl, $C_5$-$C_6$ cycloalkyl, phthalyl or methylphthalyl wherein any two R groups taken together form a saturated or unsaturated cyclic substituent.

4. The method of generating an immunologic response in a warm-blooded animal comprising administering to said animal a haloacylated bacterial endotoxin lipopolysaccharide and a haloacylated bacterial endotoxin polysaccharide covalently coupled to a protein antigen in an amount sufficient to develop an antibody response in said animal.

5. An immunizing agent in unit dosage form comprising a haloacylated bacterial endotoxin lipopolysaccharide and a haloacylated bacterial endotoxin polysaccharide covalently coupled to a protein antigen in an inert saline carrier.

* * * * *